(12) United States Patent
Sun

(10) Patent No.: US 10,704,893 B2
(45) Date of Patent: Jul. 7, 2020

(54) DEVICE FOR IN-SITU OBSERVATION OF APPARENT SPECTRUM OF WATER BODY

(71) Applicant: Zhaohua Sun, Guangzhou (CN)

(72) Inventor: Zhaohua Sun, Guangzhou (CN)

(*) Notice: Subject to any disclaimer, the term of this patent is extended or adjusted under 35 U.S.C. 154(b) by 118 days.

(21) Appl. No.: 15/730,389

(22) Filed: Oct. 11, 2017

(65) Prior Publication Data
US 2019/0072377 A1 Mar. 7, 2019

(30) Foreign Application Priority Data

Sep. 1, 2017 (CN) .......................... 2017 1 07776229

(51) Int. Cl.
| | | |
|---|---|---|
| *G01B 11/02* | (2006.01) | |
| *G01N 33/18* | (2006.01) | |
| *G01N 21/25* | (2006.01) | |
| *G01B 11/24* | (2006.01) | |

(52) U.S. Cl.
CPC .......... *G01B 11/026* (2013.01); *G01B 11/24* (2013.01); *G01N 21/255* (2013.01); *G01N 33/1886* (2013.01); *G01N 2201/0212* (2013.01); *G01N 2201/0616* (2013.01)

(58) Field of Classification Search
None
See application file for complete search history.

(56) References Cited

U.S. PATENT DOCUMENTS

| | | | | | |
|---|---|---|---|---|---|
| 3,630,161 | A | * | 12/1971 | Georgii | .................. B65D 88/78 |
| | | | | | 114/256 |
| 4,515,013 | A | * | 5/1985 | Hue | ........................ G01P 15/00 |
| | | | | | 73/170.01 |
| 6,471,854 | B1 | * | 10/2002 | Sebben | .................. B01D 17/00 |
| | | | | | 210/122 |

(Continued)

FOREIGN PATENT DOCUMENTS

DE 10351186 A1 * 6/2005 ............ F03B 13/187

OTHER PUBLICATIONS

Hu L; "Deep sea probe observation instrument, has optical fiber cable connected with multiple buoyancy rings according to certain distance in carbon fiber that is provided with propeller, camera, sensor and mechanical arm: Derwent 2013-Q81411 N 202935561"; Derwent; Oct. 12, 2012 (Year: 2012).*

(Continued)

*Primary Examiner* — Shawn Decenzo
(74) *Attorney, Agent, or Firm* — Hamre, Schumann, Mueller & Larson, P.C.

(57) ABSTRACT

A system for in-situ measurement of an apparent spectrum of a water body includes a floating device, and an optical sensing and conduction device, an electronic measurement device, a control circuit, and a power supply device which are loaded on the floating device. The floating device includes a floating body ring and an optical probe mounting frame on the floating body ring in a direction perpendicular to a ring surface. The optical probe mounting frame includes a vertical mounting assembly and a horizontal connecting (Continued)

assembly. The horizontal connecting assembly is provided radially along the ring shape of the floating body ring. One end of the horizontal connecting assembly is connected to the vertical mounting assembly and the other end thereof is connected to the floating body ring.

16 Claims, 7 Drawing Sheets

(56) References Cited

U.S. PATENT DOCUMENTS

| 8,920,652 B2* | 12/2014 | Santamaria | F17D 3/00 |
| | | | 210/170.05 |
| 2011/0068578 A1* | 3/2011 | Chervin | F03B 13/20 |
| | | | 290/53 |
| 2014/0203184 A1* | 7/2014 | Purdy | G01N 33/18 |
| | | | 250/393 |

OTHER PUBLICATIONS

Lee et al., "Robust approach to directly measuring water-leaving radiance in the field", Optical Society of America, Mar. 10, 2013; vol. 52, No. 8, pp. 1693-1701; 9 pages provided.

* cited by examiner

DEVICE FOR IN-SITU OBSERVATION OF APPARENT SPECTRUM OF WATER BODY

TECHNICAL FIELD

The present invention relates to the field of optical observation, in particular to the field of observation of apparent spectra in water color remote sensing sites, and more particularly to a device for in-situ observation of an apparent spectrum of a water body.

BACKGROUND

The water-leaving radiance ($L_w$) and the remote sensing reflectivity ($R_{rs}$) are the core parameters of ocean optics. For example, the intrinsic optical quantity, the chlorophyll concentration, the optical shallow water substratum and other parameters can be obtained by inversion from $R_{rs}$. Moreover, the on-site measured $L_w$ can be used for ground calibration, authenticity testing, and atmospheric correction of an airborne or spatial sensor.

The spectrum of the on-site measured $L_w$ has been in a 50-year history. There are three measurement methods that have been developed and implemented in the prior art, including an over-the-surface measurement method, an underwater profile measurement method and a water surface floating measurement method. Although these methods are easy to implement in the measurement site, but incapable of directly measuring $L_w$ of the water body. In addition, when $L_w$ is derived by measuring some of the relevant parameters, because there are some uncertain factors in the derivation process, the $L_w$ derived from these methods has a great error.

As described in many studies, it is not possible to accurately determine the reflectivity of a gas-water interface if the sea surface is roughened by waves when $L_w$ is estimated by using the over-the-surface measurement method, so that it is difficult to accurately remove reflected light of the surface, resulting in the introduction of huge uncertain factors in the process of deriving $L_w$. In the underwater profile measurement method, in order to derive the upward radiance to the water surface, it is necessary to obtain a correct attenuation coefficient by means of precise data processing; in practical applications, it is very difficult to accurately estimate the attenuation coefficient of propagation for highly turbid waters or vertically stratified waters, and therefore, there are also huge uncertain factors in the final derivation of $L_w$. For the surface floating measurement method, it is necessary to derive the upward radiance at 10-50 cm below the water surface as the upward radiance just at 0 cm below the water surface. Moreover, for the underwater profile measurement method and the surface floating measurement method, it is necessary to subjectively derive the water-leaving radiance $L_w$ from the upward radiance just at 0 cm below the water surface by assuming the refractive index and the cross-sectional reflectivity of water. Therefore, even if each component is measured accurately, a variety of degrees of uncertain factors will still affect the calculation of $L_w$.

At present, the water surface floating measurement method has been rarely mentioned, but there are representative instruments for the over-the-surface the measurement method and the underwater profile measurement methods. For example, representative observation instruments using the over-the-surface measurement method are HyperSAS apparent spectrum observation devices, and the like manufactured in Canada's Satlantic Company; representative observation instruments using the underwater profile measurement method are ocean optical buoys, and the like.

In summary, regardless of the kind of the observation instrument, the water-leaving radiance cannot be measured accurately as long as any of the above three measurement methods is adopted in the prior art. Therefore, it is necessary to develop a device for observation of an apparent spectrum of a water body based on a new observation method, which makes use of a method of deriving the water-leaving radiance rather than direct measurement, thereby furthest reducing the method defectors, personal errors, device investment and the difficulty in operation and maintenance, and achieving a higher observation accuracy.

SUMMARY

An objective of the present invention is to provide a novel optical observation device for a water body against the problems present in the existing apparent spectrum observation of a water body. The device may be used for directly measuring a water-leaving radiance $L_w$ of the water body, and can furthest reduce the method defects, personal errors and device errors. The precision of a remote sensing reflectivity $R_{rs}$ finally observed of the water body is improved remarkably. In addition, the device meets the technical requirements of ocean optical measurements in terms of shadows, postures, safety, ease of deployment and recovery, convenience in maintenance, etc.

The objective of the present invention is realized by the following technical solution:

First, there is provided a floating device for optical observation of a water body. The floating device comprises a floating body ring and an optical probe mounting frame provided on the floating body ring in a direction perpendicular to a ring surface. The optical probe mounting frame comprises a vertical mounting assembly and at least one horizontal connecting assembly. The horizontal connecting assembly is provided radially along the ring shape of the floating body ring, one end of the horizontal connecting assembly being connected to the outer side of the vertical mounting assembly, and the other end thereof being connected to the floating body ring, such that the vertical mounting assembly is overhung outside the ring surface of the floating body ring, and meanwhile a vertical projection of the vertical mounting assembly is located in the center of the ring surface. A ratio of an inner diameter to an outer diameter of the floating body ring is 0.80 to 0.85. The horizontal connecting assembly is elongated and the body width is much smaller than a wire diameter of the floating body ring. The floating body ring is provided with a watertight cavity which provides flotage for the whole floating device, and meanwhile is used for loading a necessary electronic device and a necessary power supply assembly. An optical probe is mounted on the optical probe mounting frame in a vertical direction.

The floating device disclosed by the invention may be used for optical observation of different water bodies. Various optical observation instruments, such as a radiance probe and an irradiance probe, may be loaded on the optical probe mounting frame. Since a position where the observation instruments are mounted is located in the center above the ring surface of the floating body ring, and the wire diameter of the floating body ring is small per se, projection shadows of the floating body ring and the probe are smaller when the radiance probe and the irradiance probe are loaded. In addition, the solar altitude is high enough, the projection shadow of the floating body ring is far from a measurement area of the probe. Compared with an existing observation device, it is unnecessary to increase the number of the instruments for ensuring the quality of data measurement, and therefore the device investment is reduced remarkably.

According to the floating device disclosed by the present invention, a forming method of the floating body ring is not limited, which may be either an integrally formed floating body ring with a cavity, or a floating body ring composed of a plurality of sections of arc-shaped structure with cavities.

In a preferred embodiment of the present invention, the floating body ring is formed by combined mounting of a plurality of independent arc-shaped structures with cavities. Therefore, the modularization of the floating body ring is realized to further increase the convenience in manufacture, transportation and maintenance of the floating device. In a further preferred embodiment of the present invention, in order to improve the modularization degree of the floating body ring, each section of the arc-shaped structure with the cavity comprises a bottom groove and a top cover which are connected in a water-tight manner to form the cavity inside; all the grooves are identical in specification and may be interchanged; all the covers are identical in shape and size, but may be provided with or not provided with water-tight joints as required.

In the same way, in order to improve the modularization of the entire floating device to meet the requirements of different observation conditions and observation environments, in a further preferred embodiment of the present invention, the horizontal connecting assembly is composed of different shapes of a plurality of porous assemblies which are in screw connection via holes, and one end, which is connected with the vertical mounting assembly, of the horizontal connecting assembly is also provided with connecting holes; a side surface of the vertical mounting assembly is provided with connecting holes different in height, by which the vertical mounting assembly is screw connection with the horizontal connecting assembly. Therefore, the heights of screw connection nodes of the optical probe mounting frame are adjustable, such that the optical probe mounted on the optical probe mounting frame has different heights under different conditions.

In another preferred embodiment of the present invention, the floating body ring is an integrally formed floating body ring with a cavity. The integrally formed floating body ring with the cavity comprises a bottom integral groove and a top integral cover which are connected in a water-tight manner. The horizontal connecting assembly of the optical probe mounting frame is in a shape of a hollow pipe, one end of the horizontal connecting assembly being fixedly connected to the integral cover, and the other end of the horizontal connecting assembly being fixedly connected to the vertical mounting assembly, thereby forming a channel that reaches the inside of the integral groove from the inside of the vertical mounting assembly by passing through the inner cavity of the horizontal connecting assembly and then through the integral cover. A cable may be arranged in the channel to connect the optical probe mounted on the vertical mounting assembly and the electronic device loaded in the integral groove. In a more preferred embodiment, an internal space of the integral groove is partitioned into a plurality of regions for regional mounting of electronic devices having different functions.

On this basis, a system for in-situ measurement of an apparent spectrum of a water body comprises the floating device disclosed by the present invention, and an optical sensing and conduction device, an electronic measurement device, a control circuit and a power supply device which are loaded on the floating device. The optical sensing and conduction device comprises an irradiance probe, a radiance probe, conducting optical fibers and a radiance probe hood, wherein the irradiance probe is vertically mounted upwards on the vertical mounting assembly of the optical probe mounting frame in the floating device. The radiance probe is vertically mounted downwards on the vertical mounting assembly of the optical probe mounting frame in the floating device. The radiance probe hood is conical, and fixedly mounted on the periphery at the bottom end of the vertical mounting assembly, and vertically extends to a position below the ring surface of the floating body ring of the floating device from a position where the radiance probe is located. The electronic measurement device, the control circuit and the power supply device are mounted in the water-tight cavity of the floating body ring of the floating device. The conducting optical fibers are arranged along the horizontal connecting assembly of the optical probe mounting frame in the floating device, and connect the radiance probe and the irradiance probe to the electronic measurement device respectively through the water-tight joints provided on the surface of the floating body ring. The electronic measurement device, the control circuit and the power supply device are electrically connected inside the water-tight cavity.

In the system for in-situ measurement of the apparent spectrum of the water body, which is preferred in the present invention, the floating device is further provided with a communication device and a positioning device. The communication device comprises a wireless waterproof communication antenna provided on the surface of the floating body ring and a wireless communication module provided in the water-tight cavity. The wireless waterproof communication antenna and the wireless communication module are electrically connected through the water-tight joints on the surface of the floating body ring. The positioning device comprises a posture sensor provided on the vertical mounting assembly of the optical probe mounting frame, a GPS module provided in the water-tight cavity and a GPS waterproof antenna provided on the surface of the floating body ring. The GPS waterproof antenna and the GPS module are electrically connected through the water-tight joints on the surface of the floating body ring. The posture sensor and the electronic measurement device are electrically connected via a water-tight cable through the water-tight joints provided on the surface of the floating body ring.

The optical probe in long-term operation in the field is susceptible to the impact of the environment and easy to be contaminated, resulting in inaccurate measurement data. In order to reduce the measurement errors caused by pollutions, in the system for in-situ measurement of the apparent spectrum of the water body as preferred in the present invention, an electric optical probe cleaning device is further provided on the vertical mounting assembly of the optical probe mounting frame in the floating device; the electric optical probe cleaning device is used for cleaning the surface of a lens of any or all of the optical probes mounted on the optical probe mounting frame.

In a further preferred embodiment of the present invention, two ends of the vertical mounting assembly are fixedly connected to a group of electric optical probe cleaning devices respectively. Each group of the electric optical probe cleaning device comprises a waterproof steering engine which is fixedly connected to the two ends of the vertical mounting assembly respectively, the waterproof steering engine comprising a circuit board and a motor. The circuit board is electrically connected to the control circuit in the water-tight cavity of the floating body ring via a water-tight control cable and receives a control signal emitted from the control circuit to further control a motor to rotate. The end part of a rotating shaft of the motor is sleeved with a strip-shaped scraping member. The strip-shaped scraping member is integrally in tight contact with the surface of the optical probe mounted on the vertical mounting assembly, and reciprocates on the surface of the lens under the driving of the motor. The electric optical probe cleaning device ensures the cleaning of a lens of a dual-channel optical probe mounted outside a cabin so as not to be affected by splashing, dust, biological attachments and the like.

In the ocean optical observation operation, the observation device is usually violent with the wave motion under terrible ocean environments, which is prone to overturning. In order to improve the overall anti-overturning capacity of the measurement system of the present invention, in a preferred embodiment of the present invention, the bottom of the floating device is further connected to a counterweight assembly for adjusting the center of gravity and the waterline of the floating device. When the buoyant centre of the floating device is located above the center of gravity, the heights of the waterline and the center of gravity of the floating device are reduced by adjusting the weight and/or size of the counterweight assembly. In a further preferred embodiment, the counterweight assembly is composed of an elongated counterweight lever and a columnar counterweight fixedly connected to one end of the counterweight lever, and the other end of the counterweight is fixedly connected to the bottom of the floating device. When the buoyant centre of the floating device is located over the center of gravity, the length-diameter ratio of the counterweight and the length of the counterweight lever may be increased to increase the anti-overturning stability of the floating body and reduce the swing angle.

In a preferred embodiment of the present invention, the radiance probe hood is a cone made of a matte black non-polar hard material, and an included angle between an axis and a generatrix of the cone is 10-15 degrees to minimize the impact of the cone itself.

In a preferred embodiment, a distance between the radiance probe and the waterline of the floating device is 4 to 8 cm, preferably 5 to 6 cm, so as to ensure that the probe may measure the radiance at the horizontal plane and not be flooded by water.

It is well known in the art that the remote sensing reflective index $R_{rs}$ of the water body is a ratio of the water-leaving radiance $L_w$ to the incident solar irradiance $E_s$. In the prior art, it is not easy to obtain the value of $R_{rs}$, with the difficulty mainly lying in that the water-leaving radiance $L_w$ may not be obtained accurately. $L_w$ cannot be measured directly in the prior art, but requires a complex derivation. For example, $L_w$ may not be measured directly by the over-the-surface observation method, but may be derived by removing reflected light of the water surface brought by sky stray light from the upward radiance over the water surface. Owing to the complicated measurement process and the empirical formula derivation process, the resulting $L_w$ value which is derived indirectly is affected by many factors such as a weather condition, a personnel operation, a device status and inherent personal errors caused by empirical formula. It is difficult to guarantee the accuracy, and further the accuracy of $R_{rs}$ is affected seriously. The underwater profile observation method can avoid the impact from reflected light of the water surface, but cannot be directly measure $L_w$. The radiance parameters of the water surface may be derived by observing a vertical profile of an upward radiance within certain water column below the water surface and then using a mathematical formula. The derivation process is still complex with a great impact from uncertain factors.

The observation system for the apparent spectrum of the water body disclosed by the present invention can realize the direct in-site observation of the apparent spectrum of the water body. In actual use, the observation system for the apparent spectrum of the water body disclosed by the present invention is carried by a mother ship to an area to be observed and put to a proper position. After the observation system floats away from an area of a shadow of the mother ship, an observation program is started remotely. During the observation process, the radiance probe is located on the vertical mounting assembly of the floating device and is always above the water surface under the action of the flotage, and a window is directed to the water surface for measuring an upward radiance. At the same time the lower edge of the cone of the hood is always just below the water surface, and can completely shield sky stray light in an observation area below the radiance probe. While measuring the upward radiance, the irradiance probe is located at the top end of the floating device, is always above the water surface under the action of the flotage and directly to the sky for acquiring data of solar irradiance $E_s$. If the posture sensor is also loaded at the same time, it may be used for synchronously acquiring posture data of the floating device. Therefore, the observation of the upward radiance value over the water surface by the radiance probe has no introduction of other interference factors, without the need for complex derivation to remove the impact from reflected light of the surface of the water body. In fact, it is pure $L_w$. Therefore, the observation device of the present invention is able to achieve the goal of a direct measurement of $L_w$ that cannot be achieved in the prior art, so that the precision of the observed $R_{rs}$ is significantly improved over the prior art. Further, more accurate water remote sensing reflectivity $R_{rs}$ may be obtained finally by removing synchronous data of abnormal postures discriminated according to the posture data.

In the device of the invention, the data acquired by the optical probe and the posture sensor may be transmitted to a control center through a variety of existing wireless transmission modes. The suitable transmission modes mainly include radio data transmission and satellite communication, for example, a signal transceiver may be provided in the control center of the mother ship, and meanwhile a radio antenna is provided on a floatable frame, thereby achieving radio data transmission.

The observation device for the apparent spectrum disclosed by the present invention may be applied indefinitely to various waters of the world, and is particularly suitable for use in marine optical observation. In marine optical observations, the device of the present invention may be applied in at least two forms: one form is to use only one set of the device to be repeatedly delivered and recovered by the mother ship at a fixed observation site for long-term, multiple observations in the same sea area; the other form is to deliver a large number of identical devices of the present invention once to waters of the world, for long-term observations for more than one year at multiple sites.

DETAILED DESCRIPTION

To make the above objective, features and advantages of the present invention more apparent, specific embodiments of the present invention will be described in detail with reference to the accompanying drawings.

Numerous specific details are set forth in the following description so as to fully understand the present invention, but the present invention may be implemented by adopting other manners otherwise than as specifically described herein. Those skilled in the art will be able to make similar generalizations without departing from the spirit of the present invention, and thus the present invention is not limited by the specific embodiments disclosed below.

Secondly, the present invention is described in detail in conjunction with the schematic drawings. In the detailed description of the embodiments of the present invention, for convenience of description, the cross-sectional view showing the structure of the device will be partially enlarged without following the general proportions. In addition, the schematic views are merely illustrative and should not be construed as limiting the protection scope of the present invention. In addition, three-dimensional spatial sizes in length, width and depth should be included in practical production.

Embodiment 1

Figure 1:
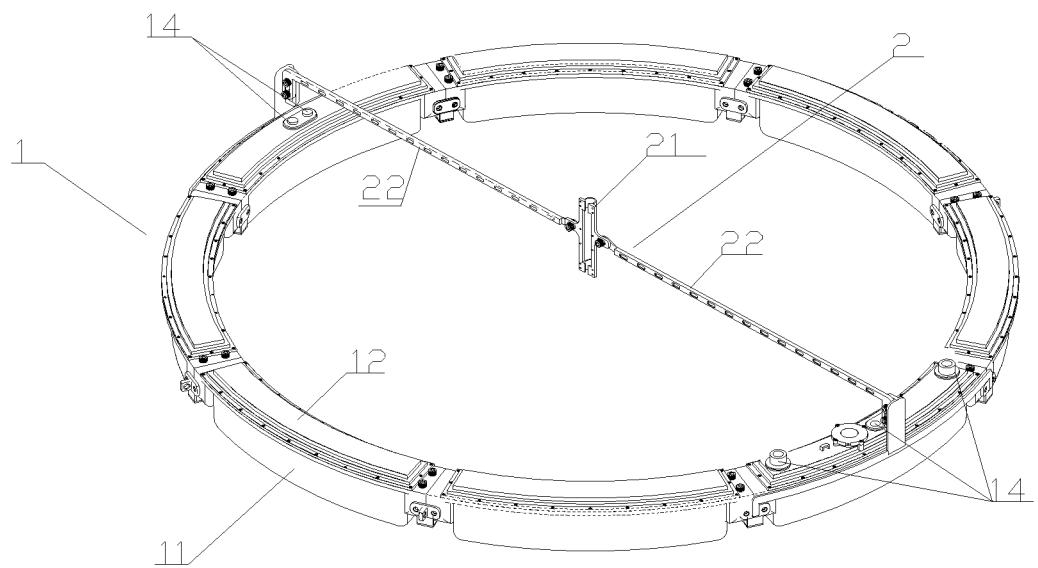
FIG. 1 is a schematic view showing the overall structure of a floating device A according to Embodiment 1.

As shown in FIG. 1, a floating device A for optical observation of a water body comprises a floating body ring 1 and an optical probe mounting frame 2 which is provided on the floating body ring in a direction perpendicular to a ring surface. The optical probe mounting frame 2 comprises a vertical mounting assembly 21 and two horizontal connecting assemblies 22. The horizontal connecting assemblies 22 are provided radially along the ring shape of the floating body ring 1. One end of each horizontal connecting assembly is fixedly connected to the outer side of the vertical mounting assembly 21, and the other end thereof is fixedly connected to the floating body ring 1, such that the vertical mounting assembly 21 is overhung outside the ring surface of the floating body ring 1, and meanwhile, a vertical projection of the vertical mounting assembly is located in the center of the ring surface. A ratio of an inner diameter to an outer diameter of the floating body ring 1 is 0.80.

Figure 2:
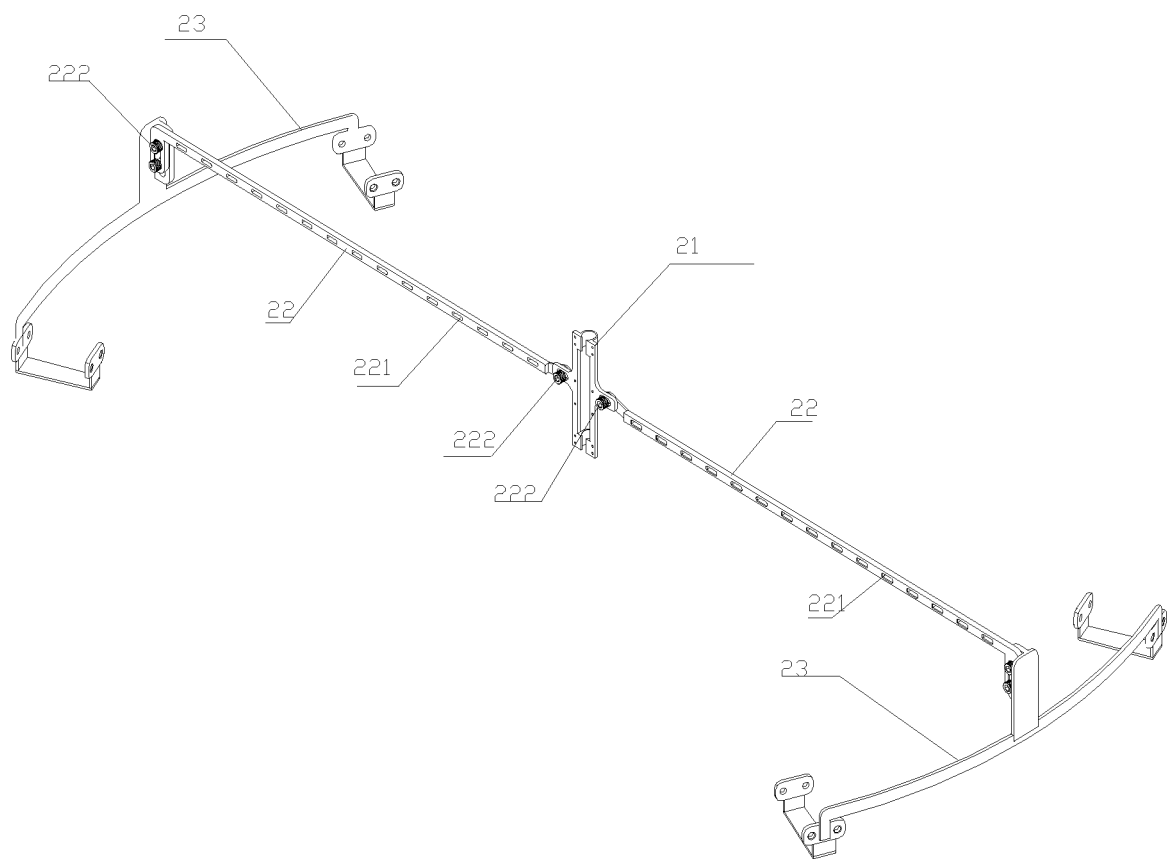
FIG. 2 is a schematic structural of an optical probe mounting frame of the floating device A according to Embodiment 1.

As shown in FIG. 2, the horizontal connecting assembly 22 is elongated and the body width is much smaller than a wire diameter of the floating body ring 1. A body and two ends of each of the horizontal connecting assemblies are provided with a plurality of holes 221, wherein the holes 221 in one end of the horizontal connecting assembly are in screw connection with a connector 23 fixed on the floating body ring 1 via screws 222, and the holes in the other end of the horizontal connecting assembly are in screw connection with the vertical mounting assembly 21 via screws 222. A side surface of the vertical mounting assembly 21 is also provided with connecting holes 221 which are used for being in screw connection with the horizontal connecting assemblies 22.

Figure 3:
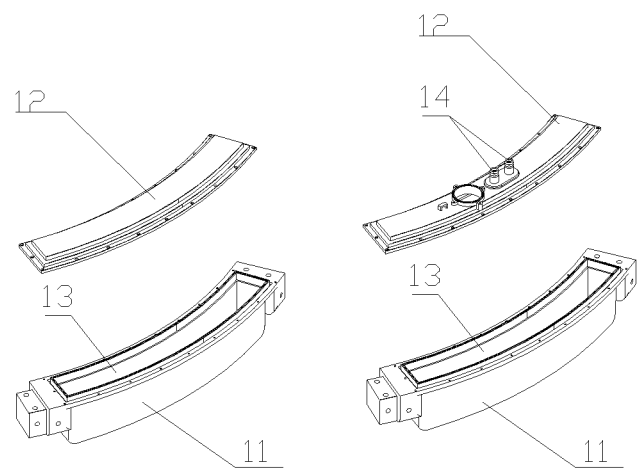
FIG. 3 is an exploded schematic view of different arc-shaped structures with cavities in a floating body ring of the floating device A according to Embodiment 1, wherein the arc-shaped structure which is not provided with a water-tight joint on a cover is located at the left side, and the arc-shaped structure which is provided with a water-tight joint on a cover is located at the right side.

As shown in FIGS. 1 and 3, the floating body ring 1 is formed by combining a plurality of sections of arc-shaped structures with cavities. Each section of the arc-shaped structure with the cavity comprises a bottom groove 11 and a top cover 12 which are connected a water-tight manner to form a water-tight cavity 13 inside. All the grooves are identical in specification and may be interchanged. All the covers are identical in shape and size, but may be provided with or not provided with water-tight joints 14 as required. The water-tight cavity provided with the water-tight joint 14 may be considered as a water-tight electronic cabin or a water-tight battery cabin, and used for placing measurement instruments and a power supply device.

Embodiment 2

Figure 4:
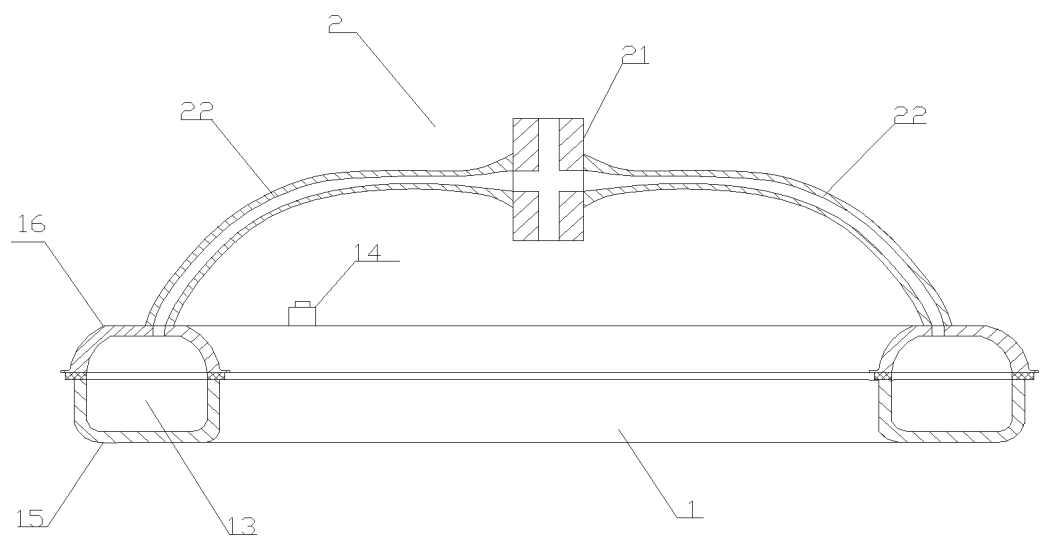
FIG. 4 is an overall longitudinal sectional schematic view of the floating device B according to Embodiment 2.

As shown in FIG. 4, a floating device B for optical observation of a water body comprises a floating body ring 1 and an optical probe mounting frame 2 which is provided on the floating body ring in a direction perpendicular to the ring surface. The optical probe mounting frame 2 comprises a vertical mounting assembly 21 and two horizontal connecting assemblies 22. The horizontal connecting assemblies 22 are provided radially along the ring shape of the floating body ring 1. One end of each horizontal connecting assembly is fixedly connected to the outer side of the vertical mounting assembly 21, and the other end thereof is fixedly connected to the floating body ring 1, such that the vertical mounting assembly 21 is overhung outside the ring surface of the floating body ring 1, and meanwhile, a vertical projection of the vertical mounting assembly is located in the center of the ring surface. A ratio of an inner diameter to an outer diameter of the floating body ring 1 is 0.85.

The floating body ring 1 is an integrally formed ring body. The floating body ring 1 comprises a bottom integral groove 15 and a top integral groove 16 which are connected in a water-tight manner to form a water-tight cavity 13 inside. Each of the horizontal connecting assemblies 22 of the optical probe mounting frame is in a shape of a hollow pipe, thereby forming a channel that reaches the inside of the integral groove 15 from the inside of the vertical mounting assembly 21 by passing through the inner cavity of the horizontal connecting assembly 22 and then through the integral cover 15. A cable may be arranged inside the channel to connect an optical probe mounted on the vertical mounting assembly 21 and an electronic device loaded in the integral groove 15.

Figure 5:
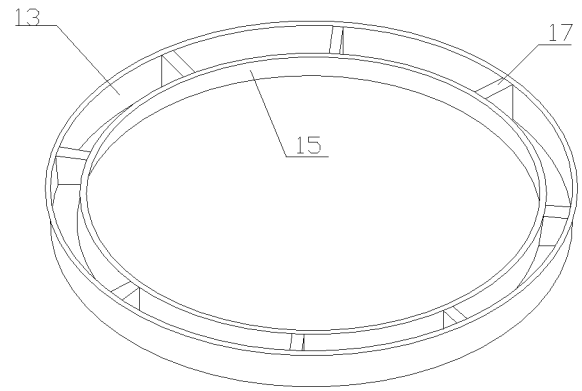
FIG. 5 is a schematic view showing the internal structure of an integral groove of the floating device B according to Embodiment 2.

As shown in FIG. 5, the water-tight cavity 13 inside the integral groove 15 is partitioned into a plurality of regions by a plurality of upright plates 17 for regional mounting of electronic devices having different functions.

Embodiment 3

Figure 6:
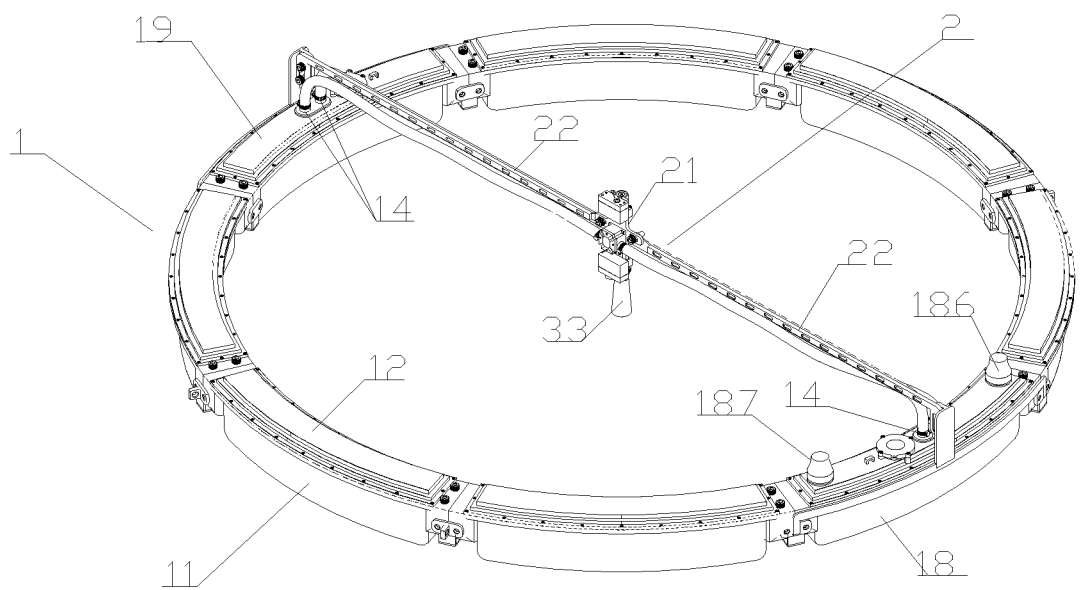
FIG. 6 is a schematic view showing an overall structure of a system for in-situ measurement of an apparent spectrum of a water body according to Embodiment 3.
Figure 7:
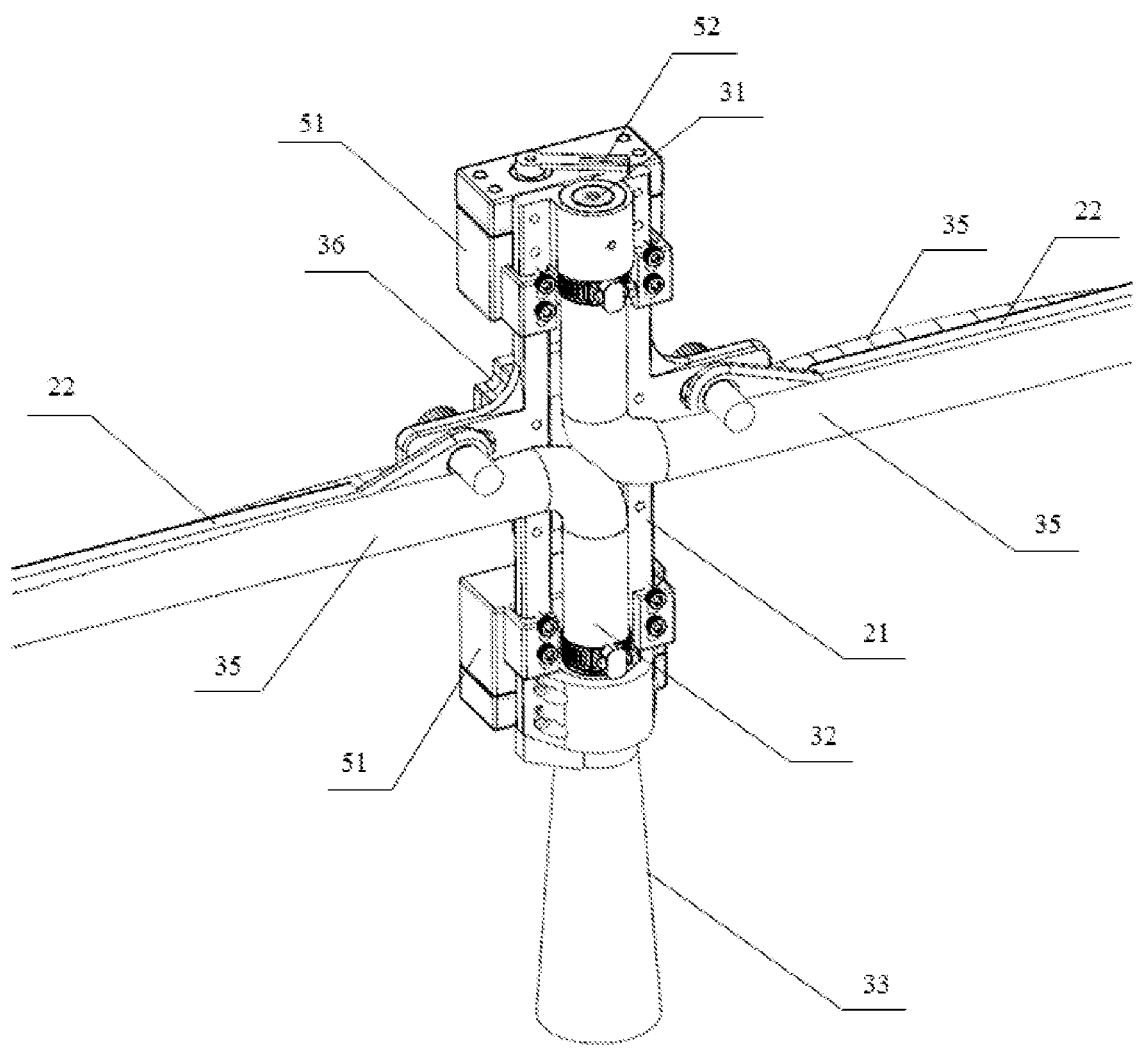
FIG. 7 and FIG. 8 are locally enlarged views of two side surfaces of a vertical mounting assembly 21 of the optical probe mounting frame in the system for in-situ measurement of the apparent spectrum of the water body according to Embodiment 3, wherein a water-tight box cover is removed from a junction box 36 in FIG. 8 to display the internal structure inside.
Figure 8:
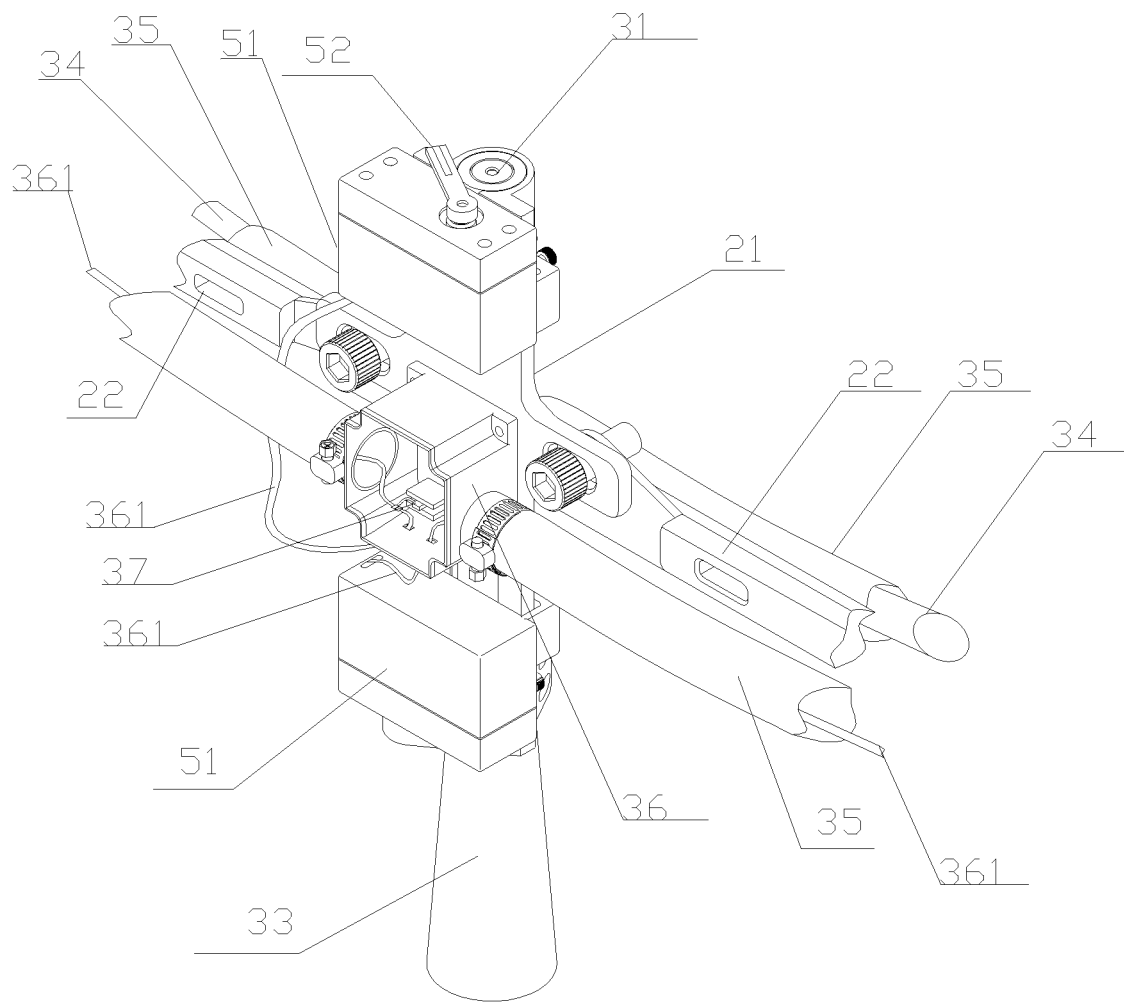

A system for in-situ measurement of an apparent spectrum of the water body comprises the floating device A according to Embodiment 1, and an optical sensing and conduction device, an electronic measurement device, a control circuit, a power supply device, a communication device and a positioning device which are loaded on the floating device A;

the electronic measuring device comprises a splitter with optical fibers, and a spectral acquisition board;

the control circuit includes a main control module and a control protection module. The main control module is the brain after awakening the whole system. The control protection module is equivalent to the brain after the dormancy of the system. After dormancy, the control right of the whole system is handed over to the control protection module, thereby reducing the power consumption of the system;

the power supply device comprises a power voltage conversion module and a rechargeable battery pack;

the communication device comprises a wireless waterproof communication antenna and a wireless communication module;

the positioning device includes a posture sensor, a GPS waterproof antenna, a GPS positioning module;

the optical sensing and conduction device comprises an irradiance probe, a radiance probe, conducting optical fibers, and a radiance probe hood;

as shown in FIGS. 6, 7 and 8, the irradiance probe 31 is vertically mounted upwards on the vertical mounting assembly 21 of the optical probe mounting frame of the floating device A (refer to FIGS. 7 and 8). The radiance probe 32 is vertically mounted downwards on the vertical mounting assembly 21 of the optical probe mounting frame of the floating device A (refer to FIG. 7). A lens of the radiance probe 32 is 6 cm higher than a waterline of the floating device A to ensure that the probe may measure the radiance at the horizontal plane, and may not be flooded with water. A conical hood 33 which is narrow in the upper part and wide in the lower part is fixedly mounted on the periphery at the bottom end of the vertical mounting assembly 21 to surround the radiance probe 32. An included angle between the axis and generatrix of the hood 33 is 10 to 15 degrees to minimize the affect of the shadow of the cone itself. The hood 33 vertically extends to a position below the ring surface of the floating body ring from the radiance probe 32. Two strands of the conducting fibers 34 are wrapped with a water-tight hose 35 respectively. One ends of the conducting optical fibers are respectively connected to the radiance probe 32 and the irradiance probe 31 on the vertical mounting assembly 21, and are then arranged along the horizontal connecting assemblies 22 towards two directions. The holes in the horizontal connecting assemblies 22 may be used for fixing the water-tight hoses 25. The other ends of the conducting optical fibers enter the water-tight electronic cabin 18 and the water-tight battery cabin 19 through the water-tight joints 14 respectively. A wireless waterproof communication antenna 186 and a PGS waterproof antenna 187 are provided outside the water-tight electronic cabin 18 of the floating body ring 1.

As shown in FIG. 8, the upper end and the lower end of the vertical mounting assembly 21 are fixedly connected to a group of electric optical probe cleaning devices respectively. Each group of the electric optical probe cleaning device comprises a waterproof steering engine 51 which is fixedly connected to two ends of the vertical mounting assembly 21 respectively. Each of the waterproof steering engines 51 is internally provided with a circuit board and a motor. Waterproof control cables 361 of the two circuit boards enter the junction box 26 after being led from the steering engines 51 respectively, then reach the water-tight joints 14 at two ends of the floating body ring 1 respectively via of the two water-tight hoses 35 communicated with the junction box 36, and enter into the water-tight electronic cabin 18 and the water-tight battery cabin 19 at two ends, and are then electrically connected to the control circuit to receive a control signal emitted from the control circuit to further control the motor to rotate. The end part of a rotating shaft of the motor is sleeved with a rubber brush strip 52 which is integrally in tight contact with the surface of the lens of the optical probe mounted on the vertical mounting assembly 21 and may reciprocate in a sector-shaped manner on the surface of the lens under the driving the steering engines 51. The electric optical probe cleaning device ensures the cleaning of a probe of a dual-channel optical probe mounted outside the cabin so as not to be affected by splashing, dust, biological attachments and the like. The junction box 36 is internally provided with a posture sensor 37, which enters the water-tight electronic cabin 18 through a power wire and a lead wire via the water-tight hoses 35 and the water-tight joints 14 to connect the control protection module and a power voltage conversion module.

Figure 9:
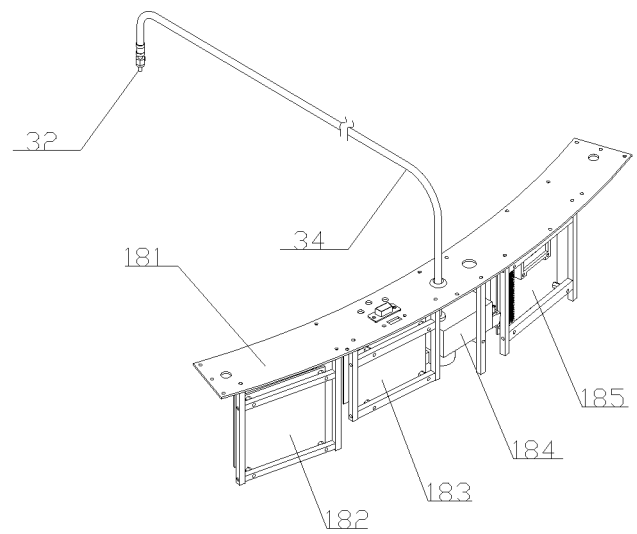
FIG. 9 and FIG. 10 are mounting diagrams of internal devices of a water-tight electronic cabin 18 and a water-tight battery cabin 19 of the system for in-situ measurement of the apparent spectrum of the water body respectively according to Embodiment 3.

As shown in FIG. 9, various devices, including a control protection and power voltage conversion integrated module 182, a radiance spectrum acquisition board 183, a radiance splitter 184 and a main control module 185, are mounted together inside the water-tight electronic cabin 18 connected with the radiance probe 32, in an integrated manner through a mounting panel 181. The optical fiber 34 connected with the radiance probe 32 is connected with the radiance splitter 184 after entering the water-tight electronic cabin 18. The control protection and power voltage conversion integrated module 182 is further provided with a radio communication module and a PGS positioning module which are electrically connected with the wireless waterproof communication antenna 186 and the PGS waterproof antenna 187 provided outside the water-tight electronic cabin 18, respectively.

Figure 10:
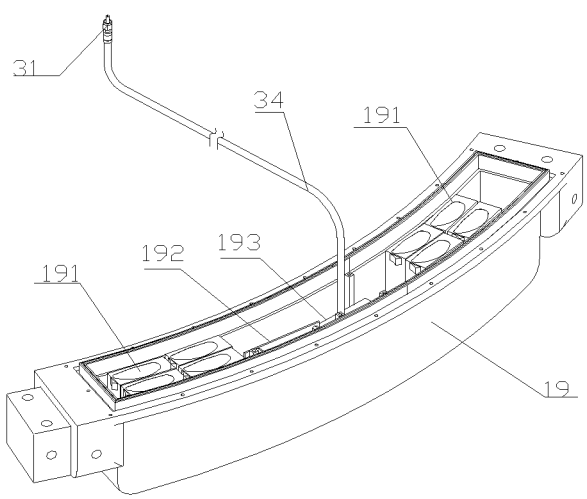

As shown in FIG. 10, the rechargeable battery pack 191, the irradiance splitter 193 and the irradiance spectrum acquisition board 192 are mounted in the water-tight battery cabin 19 connected to the irradiance probe 31. The optical fiber 34 connected to the irradiance probe 31 is connected to the irradiance splitter 193 after entering the water-tight battery cabin 19.

In the device of the present embodiment, the inner and outer surfaces of all the other assemblies except the optical probe are coated with a matte black non-polar coating.

Embodiment 4

Figure 11:
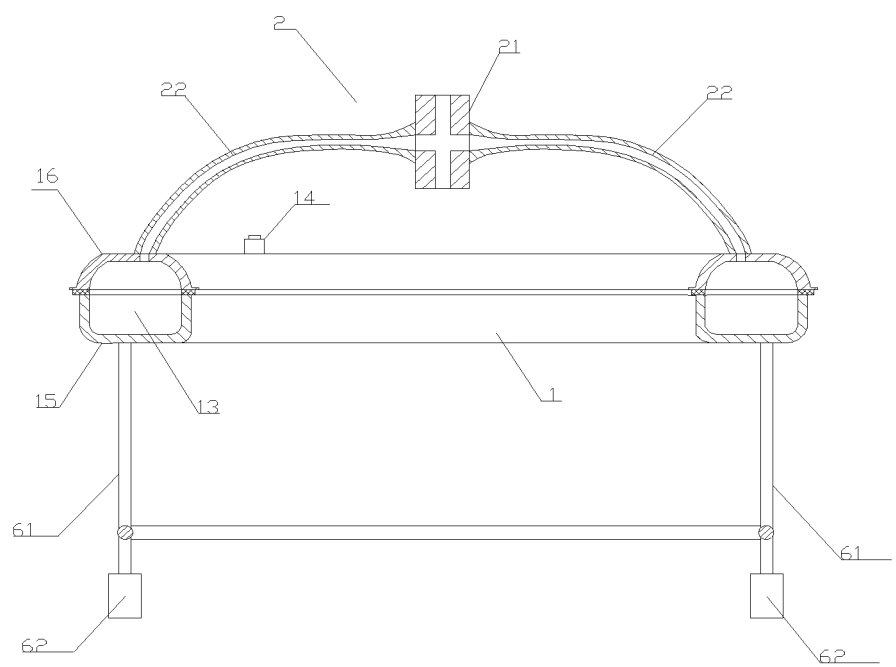
FIG. 11 is a sectional view showing an overall structure of the floating device of the system for in-situ measurement of the apparent spectrum of the water body according to Embodiment 4, which mainly displays the composition of a counterweight assembly.

Based on the floating device B disclosed by Embodiment 2, an optical sensing and conducting device, an electronic measurement device, a control circuit, a power supply device, a communication device, and a positioning device are loaded on the floating device B. The mounting position and manner are substantially the same as those of Embodiment 3. In addition, as shown in FIG. 11, a counterweight assembly is fixedly connected to the bottom of the floating device B, wherein the counterweight assembly is composed of an elongated counterweight lever 61 and a columnar counterweight 62 fixedly connected to one end of the counterweight lever. The other end of the counterweight lever 61 is fixedly connected to the bottom of the floating body ring 1. When the buoyant centre of the floating device B is located above the center of gravity, the length-diameter ratio of the counterweight 62 and the length of the counterweight 61 may be increased to increase the overall anti-overturning stability of the floating device B and reduce the swing angle.

The invention claimed is:

1. A floating device for optical observation of a water body, comprising:
   a floating body ring having a water-tight cavity for loading an electronic device and a power supply assembly, the water-tight cavity configured to provide flotage for the whole floating device, a ratio of an inner diameter to an outer diameter of the floating body ring being 0.80 to 0.85; and
   an optical probe mounting frame provided on the floating body ring in a direction perpendicular to a ring surface of the floating body ring; the optical probe mounting frame comprising:
      a vertical mounting assembly, and
      a horizontal connecting assembly having a first end and a second end, the horizontal connecting assembly provided radially along the ring shape of the floating body ring, the first end being connected to an outer side of the vertical mounting assembly and the second end being connected to the floating body ring, such that the vertical mounting assembly is radially positioned within the inner diameter of the floating body ring, and the horizontal connecting assembly being elongated with a body width smaller than a wire diameter of the floating body ring; and
   an optical probe vertically mounted on the optical probe mounting frame.

2. The floating device according to claim 1, wherein the floating body ring is formed by combined mounting of a plurality of sections of independent arc-shaped structures with cavities.

3. The floating device according to claim 2, wherein each section of the arc-shaped structure with the cavity comprises a bottom groove and a top cover which are connected in a water-tight manner to form the cavity inside, all the grooves are identical in form, all the covers are identical in shape and size except for being provided with one or more optional water-tight joints.

4. The floating device according to claim 1, wherein, the first end of the horizontal connecting assembly including connecting holes, and a side surface of the vertical mounting assembly including connecting holes with differing heights, and the vertical mounting assembly being in screw connection with the horizontal connecting assembly via the connecting holes in the horizontal connecting assembly and the connecting holes of the vertical mounting assembly.

5. The floating device according to claim 1, wherein the floating body ring is an integrally formed floating body ring with a cavity, the integrally formed floating body ring with the cavity comprises a bottom integral groove and a top integral cover which are connected in a water-tight manner,
the horizontal connecting assembly of the optical probe mounting frame is in a shape of a hollow pipe, the second end of the horizontal connecting assembly being fixedly connected to the integral cover, and the second end of the horizontal connecting assembly being fixedly connected to the vertical mounting assembly, thereby forming a channel that reaches the inside of the integral groove from the inside of the vertical mounting assembly by passing through the inner cavity of the horizontal connecting assembly and then through the integral cover.

6. The floating device according to claim 5, wherein an internal space of the integral groove is partitioned into a plurality of regions for regional mounting of electronic devices having different functions.

7. A system for in-situ measurement of an apparent spectrum of a water body, comprising:
   the floating device according to claim 1; and
   an optical sensing and conduction device loaded on the floating device, the optical sensing and conduction device comprising an irradiance probe vertically mounted upwards on the vertical mounting assembly of the optical probe mounting frame in the floating device, a radiance probe vertically mounted downwards on the vertical mounting assembly of the optical probe mounting frame in the floating device, conducting optical fibers, and a radiance probe hood that is conical, fixedly mounted on the periphery at the bottom end of the vertical mounting assembly, and vertically extends to a position below the ring surface of the floating body ring of the floating device;
   an electronic measurement device, a control circuit, and a power supply device loaded on the floating device, mounted in the water-tight cavity of the floating body ring of the floating device, and electrically connected inside the water-tight cavity, wherein
   the conducting optical fibers are arranged along the horizontal connecting assembly of the optical probe mounting frame in the floating device, and connect the radiance probe and the irradiance probe to the electronic measurement device respectively through water-tight joints provided on the surface of the floating body ring.

8. The system for in-situ measurement of the apparent spectrum of the water body according to claim 7, wherein the floating device comprises:
   a communication device comprising a wireless waterproof communication antenna provided on the surface of the floating body ring and a wireless communication module provided in the water-tight cavity, the wireless waterproof communication antenna and the wireless communication module being electrically connected through the water-tight joints on the surface of the floating body ring, and
   a positioning device comprising a posture sensor provided on the vertical mounting assembly of the optical probe mounting frame, a GPS module provided in the water-tight cavity and a GPS waterproof antenna provided on the surface of the floating body ring; the GPS waterproof antenna and the GPS module are electrically connected through the water-tight joints on the surface of the floating body ring, and the posture sensor and the electronic measurement device are electrically connected via a water-tight cable through the water-tight joints provided on the surface of the floating body ring.

9. The system for in-situ measurement of the apparent spectrum of the water body according to claim 7, wherein an electric optical probe cleaning device is further provided on the vertical mounting assembly of the optical probe mounting frame in the floating device, the electric optical probe cleaning device is used for cleaning the surface of a lens of any or all of the optical probes mounted on the optical probe mounting frame.

10. The system for in-situ measurement of the apparent spectrum of the water body according to claim 9, wherein two ends of the vertical mounting assembly are fixedly connected with a group of electric optical probe cleaning devices respectively, each group of the electric optical probe cleaning device comprises a waterproof steering engine which is fixedly connected to the two ends of the vertical mounting assembly respectively, the waterproof steering engine comprising a circuit board and a motor, the circuit board being electrically connected to the control circuit in the water-tight cavity of the floating body ring via a water-tight control cable and receives a control signal emitted from the control circuit to further control a motor to rotate wherein an end part of a rotating shaft of the motor is sleeved with a strip-shaped scraping member, the strip-shaped scraping member is integrally in tight contact with the surface of the lens of the optical probe mounted on the vertical mounting assembly, and reciprocates on the surface of the lens under the driving of the motor.

11. The system for in-situ measurement of the apparent spectrum of the water body according to claim 7, wherein the bottom of the floating device is further connected to a counterweight assembly which is used for adjusting the center of gravity and the waterline of the floating device, the counterweight assembly comprising an elongated counterweight lever and a columnar counterweight fixedly connected to one end of the counterweight lever, and the other end of the counterweight lever is fixedly connected to the bottom of the floating device.

12. The system for in-situ measurement of the apparent spectrum of the water body according to claim 7, wherein the radiance probe hood is a cone made of a matte black non-polar hard material, and an included angle between an axis and a generatrix of the cone is 10-15 degrees.

13. The system for in-situ measurement of the apparent spectrum of the water body according to claim 7, wherein a distance between the radiance probe and the waterline of the floating device is 4 to 8 cm.

14. The floating device according to claim 1, a vertical projection of the vertical mounting assembly is located in the center of the ring surface.

15. The floating device according to claim 1, wherein the vertical mounting assembly is positioned vertically higher than the floating body ring.

16. The floating device according to claim 1, wherein the floating body ring is configured to float on the water body, and the optical probe is vertically mounted on the optical probe mounting frame to be above the water body.

* * * * *